United States Patent
Carlisle

(10) Patent No.: US 9,988,509 B2
(45) Date of Patent: Jun. 5, 2018

(54) CELLULOSE CYANOACRYLATE AND METHOD OF EMPLOYMENT

(71) Applicant: Richard S. Carlisle, Waddington, NY (US)

(72) Inventor: Richard S. Carlisle, Waddington, NY (US)

( * ) Notice: Subject to any disclaimer, the term of this patent is extended or adjusted under 35 U.S.C. 154(b) by 0 days. days.

(21) Appl. No.: 15/238,748

(22) Filed: Aug. 17, 2016

(65) Prior Publication Data

US 2018/0051146 A1  Feb. 22, 2018

(51) Int. Cl.

| | |
|---|---|
| *A61L 15/16* | (2006.01) |
| *A61L 31/04* | (2006.01) |
| *C08J 5/24* | (2006.01) |
| *A61F 2/28* | (2006.01) |
| *A61L 15/12* | (2006.01) |
| *A61L 15/14* | (2006.01) |
| *D21H 11/00* | (2006.01) |
| *C09J 7/00* | (2018.01) |

(52) U.S. Cl.
CPC .............. *C08J 5/24* (2013.01); *A61F 2/2846* (2013.01); *A61L 15/125* (2013.01); *A61L 15/14* (2013.01); *C09J 7/00* (2013.01); *D21H 11/00* (2013.01); *C08J 2301/02* (2013.01); *C08J 2335/04* (2013.01); *C09J 2401/00* (2013.01); *C09J 2433/00* (2013.01)

(58) Field of Classification Search
CPC ......... A61K 9/70; A61L 15/28; A61L 31/042; A61L 31/16; C08L 1/04; Y10T 442/40; Y10T 442/3854; Y10T 442/674
USPC ........ 442/286, 444, 304, 394; 156/281, 336; 604/304; 606/60
See application file for complete search history.

(56) References Cited

U.S. PATENT DOCUMENTS

| | | | | |
|---|---|---|---|---|
| 3,958,069 | A * | 5/1976 | Gaylord ................ | B27K 3/156 156/334 |
| 4,743,468 | A * | 5/1988 | Jimenez ................ | B29C 73/02 156/94 |
| 6,500,777 | B1 * | 12/2002 | Wiseman ............... | A61K 9/70 156/281 |
| 2003/0157268 | A1 * | 8/2003 | Gutowski ............. | B27K 3/346 427/532 |
| 2006/0004314 | A1 * | 1/2006 | McCarthy .......... | A61F 13/00034 602/43 |
| 2007/0291345 | A1 * | 12/2007 | Kumar .................... | B29C 55/12 359/241 |
| 2008/0098935 | A1 * | 5/2008 | Roth .................. | B65D 19/0073 108/57.17 |
| 2010/0210745 | A1 * | 8/2010 | McDaniel ............ | C09D 5/008 521/55 |

FOREIGN PATENT DOCUMENTS

DE  202012002052 U1 *  6/2012  .............. C08J 5/24

* cited by examiner

*Primary Examiner* — Pedro Philogene

(57) ABSTRACT

Cellulose cyanoacrylate is employed either to bond two surfaces or to duplicate the shape of a three-dimensional object. The method is carried out by applying a release material to the object to be duplicated, applying a sheet of cellulosic material formed of wood fibers onto the three dimensional object, then saturating the sheet of cellulosic material with a cyanoacrylate glue and permitting the saturated sheet to cure. The resulting product duplicates the shape of the object. Two surfaces may be bonded by placing a sheet of cellulosic material between the two surfaces and applying the cyanoacrylate glue to edges of the sheet until saturated and allowing it to cure. Paper toweling may favorably be employed as the cellulosic material. This material may also be employed in bone or tooth repair. A break or fracture in an article can be repaired by positioning a sheet of cellulosic material over the break, saturating it with cyanoacrylate glue, and holding the saturated sheet in place with a releasable film. Irritating fumes may be suppressed by covering the saturated cellulosic material with a release film.

5 Claims, No Drawings

CELLULOSE CYANOACRYLATE AND METHOD OF EMPLOYMENT

BACKGROUND OF THE INVENTION

An invention is provided for repairing a wide variety of broken items made of plastic, wood or metal and is useful for copying or forming original three-dimensional prototypes and art objects similar to the methodology of fiberglass.

BRIEF SUMMARY OF THE INVENTION

The method involves employing a new compound called cellulose cyanoacrylate formed by saturating fibrous sheets of cellulosic material, e.g., including cotton and paper toweling made of wood fibers, with cyanoacrylate glue including one or more of cyano-methyl, cyano-ethyl and cyano-octyl acrylates.

DETAILED DESCRIPTION OF THE INVENTION

The cyanoacrylate-saturated cellulose can be used as an overlay on a broken area of anything in need of repair and held in place momentarily with a thin film of a release material such as polyethylene that does not adhere to the glue-saturated cellulose.

The saturated cellulose can be used as an overlay on a broken or cracked area of nearly any item. The saturated cellulose sheet can be held in place momentarily using a thin film of a release material, such as polyethylene that does not adhere to the glue-saturated cellulose. While serving for temporary retention, the release material facilitates manipulating the shape of the cellulose before hardening, by applying pressure by manual or mechanical means. The release film also plays an important role in preventing emission of irritating fumes and vapors that form during the exothermic reaction between the cellulose and the cyanoacrylate compounds.

Additionally, assuming it does not disrupt the eventual configuration of the repaired object, one or several layers of cellulose sheet—preferably paper toweling—can be placed between the surfaces to be joined and then holding the pieces together add enough cyanoacrylate glue, e.g., on the edges, to soak through the cellulose, which in itself in some cases can be sufficient as a repair without need for an exterior overlay.

To duplicate a three-dimensional object a layer of releasable film is placed around it or a silicone spray applied, followed by a cellulose sheet that is then saturated in place with cyanoacrylate glue and then another external layer of releasable film is added through which to press the cellulose snugly around the shape being duplicated. After cure, the resulting cellulose cyanoacrylate product can be removed and can be employed to duplicate the shape of the three-dimensional object.

A kit or combination for the repair of cracked or fractured articles can include one or more sheets of cellulosic material, e.g. an absorbent paper or similar wood product; a container of any type of cyanoacrylate glue; and one or more sheets of flexible film, e.g., a polyethylene film which does not adhere to the cured cyanoacrylate. This kit can also be used to duplicate the shape of a three-dimensional article or similar structure.

The advantages of the invention include:
1) Very brief cure or hardening times—ordinarily faster than thirty seconds—compared to epoxy times of one to several minutes.
2) Extreme tolerance to moisture, allowing it to function as a dental repair material as well as a great variety of underwater applications.
3) Pleasant pearl-like translucent appearance.
4) Very light weight-to-strength ratio.
5) Flexible and spring-like consistency.
6) Readily made in any color.
7) Very hard, abrasion-resistant surface.
8) Can be used for orthopedic work to repair and/or reinforce bones, i.e., at a fracture site. In many cases this technique can be used after taking the usual steps to make the wound area sterile and surgically making the fracture site available, to avoid the use of plates, pins, or screws. This technique includes repositioning and wrapping a bone fracture with two layers of paper towel or similar cellulose sheet, saturating with cyanoacrylate, and adding separately two additional layers at a time to achieve a desired strength. The cellulose sheet can be of a width between four and fifty millimeters and a thickness of one-half millimeter up to three millimeters. At each stage, the saturated layer or layers are covered with a release film and gentle pressure can be applied to exclude air pockets or bubbles and also to shape the material. Before closing up the wound site the release material is removed. The repair can be left intact indefinitely, allowing the bone to knit and thereafter the inert repair material may be left permanently in place, with the end result being a bone that is stronger than the original. In most cases there would be no need for an outer cast or splint. This technique may also be used for tooth repair.
9) Any irritant vapor or fumes can be controlled easily. During the relatively short cure period, after infusing the cellulose material with the cyanoacrylate compound(s), any vapors can be confined by covering the materials with a film of a non-pervious material which can be removed after the components have reacted sufficiently. This covering may be a release film.

Many variations of this process are possible, and the scope of the invention is to be measured by the appended claims.

I claim:

1. A cellulose cyanoacrylate compound, comprising a waterproof composition of matter formed by saturating fibrous cellulosic material selected from the group consisting of cotton and sheets of cellulose substantially comprising wood fibers, with liquid cyanoacrylate glue.

2. The compound of claim 1 wherein the glue is selected from the group consisting of one or more of cyano-methyl, cyano-ethyl and cyano-octyl acrylates.

3. The compound of claim 1 having properties of high rigidity and high abrasion resistance.

4. The compound of claim 1 shaped while curing with pressure applied through a layer of flexible material that is releasable from the cured surface.

5. The compound of claim 1 applied as a support system for repair of a bone fracture.

* * * * *